US010143579B2

(12) United States Patent
Mueller et al.

(10) Patent No.: US 10,143,579 B2
(45) Date of Patent: Dec. 4, 2018

(54) WRIST BRACE

(71) Applicant: Mueller Sports Medicine, Inc., Prairie du Sac, WI (US)

(72) Inventors: Brett Mueller, Middleton, WI (US); Zhaodong Max Li, Lodi, WI (US)

(73) Assignee: Mueller Sports Medicine, Inc., Prairie du Sac, WI (US)

( * ) Notice: Subject to any disclaimer, the term of this patent is extended or adjusted under 35 U.S.C. 154(b) by 289 days.

(21) Appl. No.: 14/751,108

(22) Filed: Jun. 25, 2015

(65) Prior Publication Data

US 2015/0374528 A1     Dec. 31, 2015

Related U.S. Application Data

(60) Provisional application No. 62/016,741, filed on Jun. 25, 2014.

(51) Int. Cl.
*A61F 5/00* (2006.01)
*A61F 5/01* (2006.01)

(52) U.S. Cl.
CPC .................. *A61F 5/0118* (2013.01)

(58) Field of Classification Search
CPC ...... A61F 5/013; A61F 5/0118; A61F 5/0102; A61F 5/0106; A61F 5/0123; A61F 5/019; A61F 5/0111; A61F 5/0127; A61F 5/058; A61F 5/0585; A61F 5/05858; A61F 5/05866; A61F 5/00; A61F 5/01; A61F 5/04; A63B 71/14; A63B 71/141–71/148; A41D 19/01588
USPC ................ 602/20–27; 128/879; 473/62, 205; 2/161.1, 162; D24/190–192
See application file for complete search history.

(56) References Cited

U.S. PATENT DOCUMENTS

| | | | | |
|---|---|---|---|---|
| 4,013,070 A | * | 3/1977 | Harroff | A61F 5/0109 602/21 |
| 5,695,453 A | * | 12/1997 | Neal | A61F 5/0118 602/21 |
| 5,749,841 A | * | 5/1998 | Moore | A61F 5/0118 602/20 |
| 6,190,344 B1 | * | 2/2001 | Bobroff | A61F 5/0102 602/21 |
| 6,328,706 B1 | | 12/2001 | Yattavong | |
| 6,398,748 B1 | * | 6/2002 | Wilson | A61F 5/0118 128/869 |
| 7,033,331 B1 | * | 4/2006 | Hely | A61F 5/0118 128/878 |
| 7,318,812 B2 | * | 1/2008 | Taylor | A61F 5/0118 602/21 |

(Continued)

FOREIGN PATENT DOCUMENTS

| | | | | |
|---|---|---|---|---|
| FR | 2990344 A1 | * | 11/2013 | ............. A61F 5/0118 |
| WO | WO 2006084220 A2 | * | 8/2006 | ........... A61F 5/0106 |

OTHER PUBLICATIONS

FR 2990344—English Translation (Nov. 2013) Frenay; Patrick.*

*Primary Examiner* — Kim M Lewis
(74) *Attorney, Agent, or Firm* — Rick L. Abegglen (57) ABSTRACT

A wrist brace for use by athletes or others requiring protection and support of the elbow. The wrist brace includes a base and two external straps for fastening the base to the wrist of a person, and a third strap located either on the inside or the outside of the base for pulling a support splint into the wrist when worn.

2 Claims, 13 Drawing Sheets

(56) References Cited

U.S. PATENT DOCUMENTS

| | | | |
|---|---|---|---|
| 7,976,487 B2* | 7/2011 | Gramza | A61F 5/0104 602/20 |
| 8,235,927 B2* | 8/2012 | Bauerfeind | A61F 5/0118 602/20 |
| 2006/0287626 A1* | 12/2006 | Bennett | A61F 5/0118 602/22 |
| 2007/0225630 A1* | 9/2007 | Wyatt | A61F 5/0118 602/21 |
| 2009/0082708 A1* | 3/2009 | Scott | A61F 5/0118 602/21 |

* cited by examiner

WRIST BRACE

CROSS REFERENCE TO RELATED APPLICATIONS

This application claims priority to provisional application No. 62/016,741 filed Jun. 25, 2014, the disclosure of which is incorporated herein by reference in its entirety for continuity of disclosure.

FIELD OF THE INVENTION

This invention relates generally to the field of articles worn by persons to reduce the likelihood, severity, or exacerbation of injury to the body, and more specifically to the field of braces worn on the wrist.

BACKGROUND OF THE INVENTION

Flexible wrist braces are used by athletes and other persons engaged in vigorous physical activity to protect the elbow from injury and to avoid exacerbation of existing injury.

Devices to protect the wrist against abnormal motions have been used for many years, in a variety of specific embodiments which vary in their abilities to protect against the different types of abnormal motions. However, the protections afforded by these devices against abnormal motion are often accompanied by a reduction in range or ease of normal motion, and may be accompanied by other undesirable aspects such as poor performance, added weight, difficulty of application, fit, cost, and/or appearance.

For these reasons, there has long been motivation to find an improved wrist brace which can protect and support the wrist without affecting the range or ease of normal motion, while avoiding the undesirable aspects of prior art devices.

SUMMARY OF THE INVENTION

In a first embodiment, a wrist brace according to the present invention includes a base and a pair of outside fastening straps that pass through apertures in the base to hold the brace on the wrist of a person. A third fastening strap has an end permanently fastened to the interior surface of the base, extending between the base and a semi-rigid or flexible splint adjacent to the wrist and then passing through an aperture in the base. Tension applied to the third strap can pull the splint closer to the wrist. An outside stay can also be provided for additional support.

In an alternate embodiment, a wrist brace according to the present invention includes a base and a pair of outside fastening straps, with a third fastening strap permanently fastened to the exterior surface of the base and pressing against the exterior surface of the base and a semi-rigid or flexible splint adjacent to the wrist. The third strap can pull the splint closer to the wrist.

Further objects, features, and advantages of the invention will be apparent from the following detailed description when taken in conjunction with the accompanying drawings.

DETAILED DESCRIPTION OF THE INVENTION

Figure 1A:
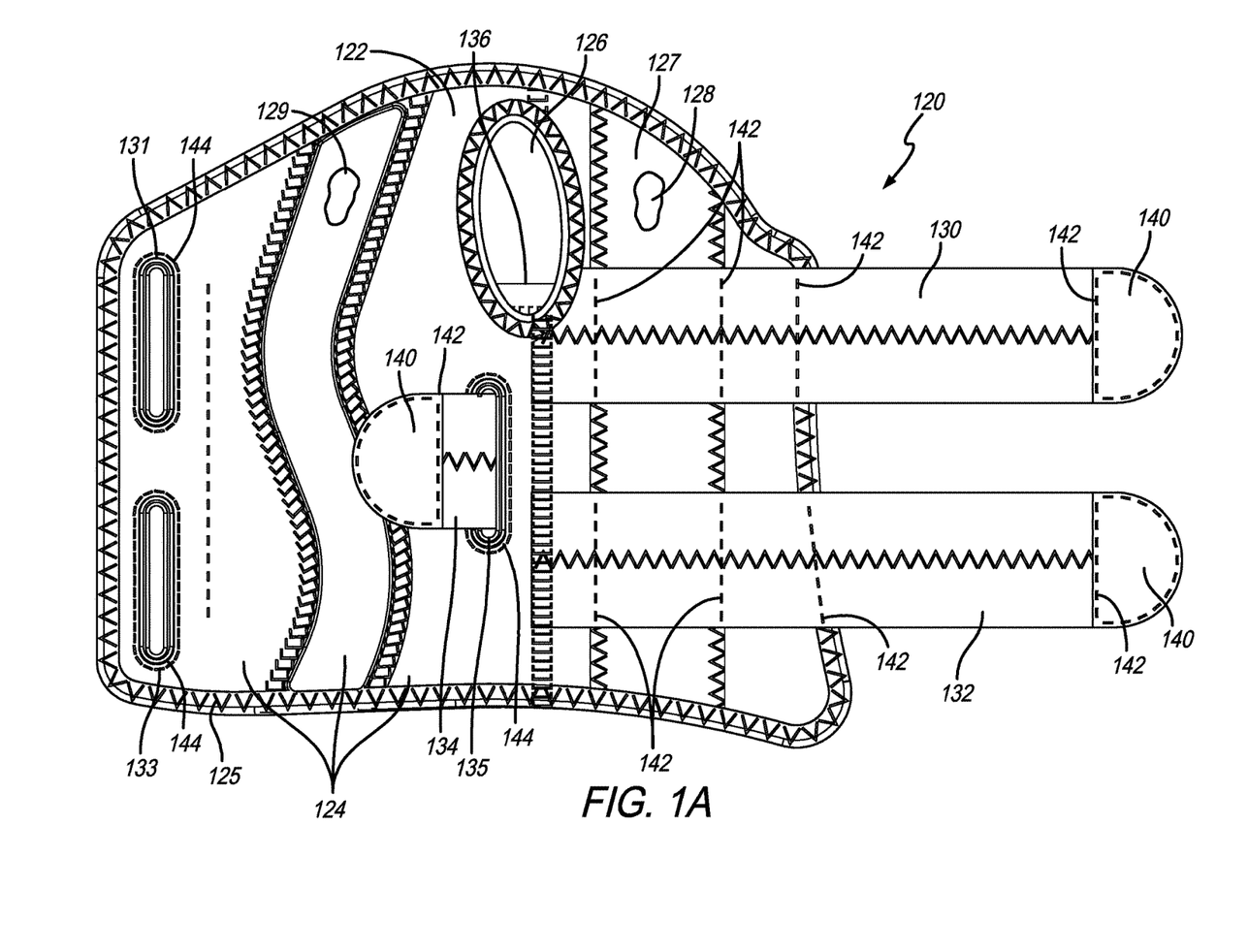
FIG. 1A is a plan view of a wrist brace according to the invention, laid flat to expose the exterior surface of the brace.
Figure 1B:
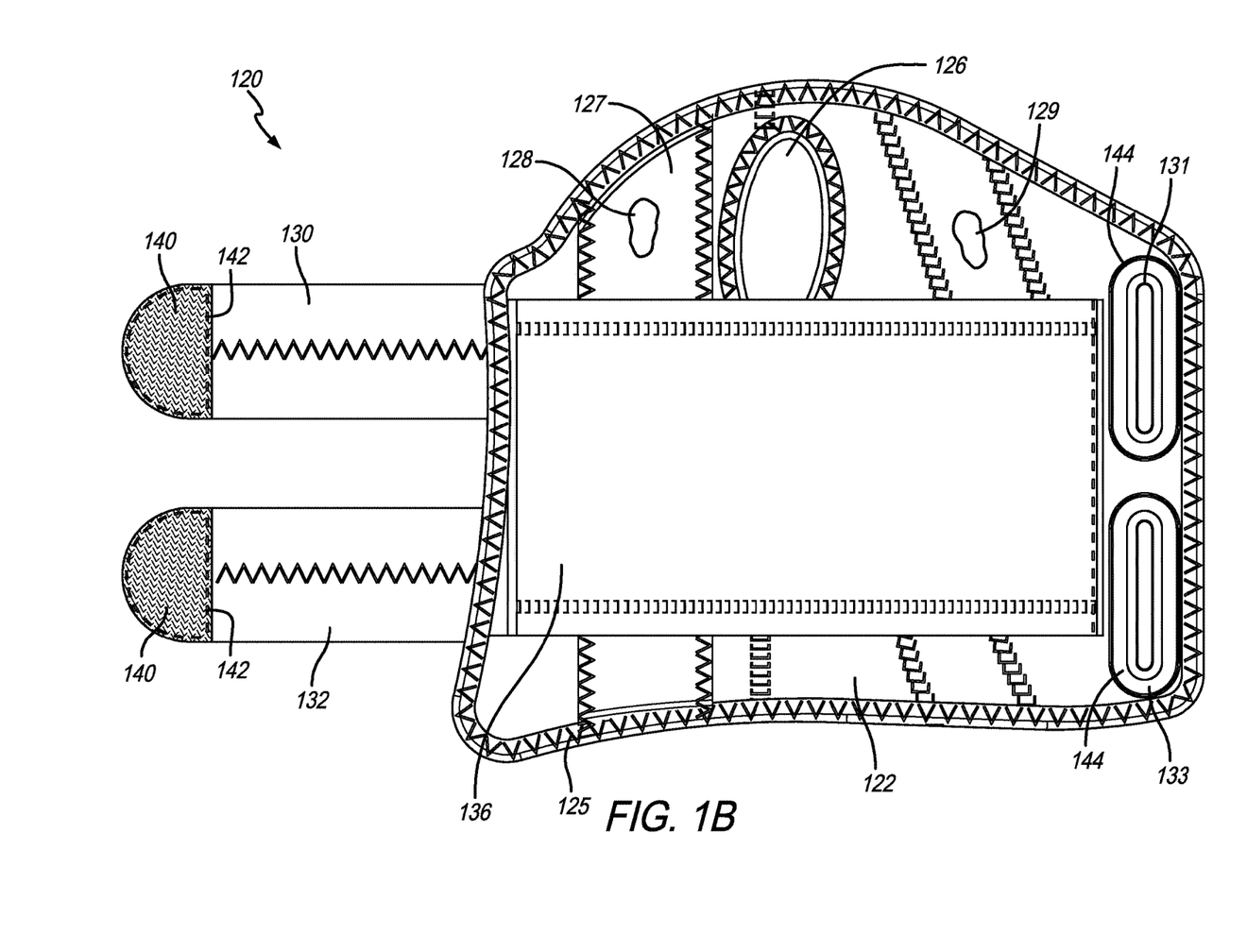
FIG. 1B is a plan view of the wrist brace of FIG. 1A, laid flat to expose the interior surface of the brace.
Figure 1C:
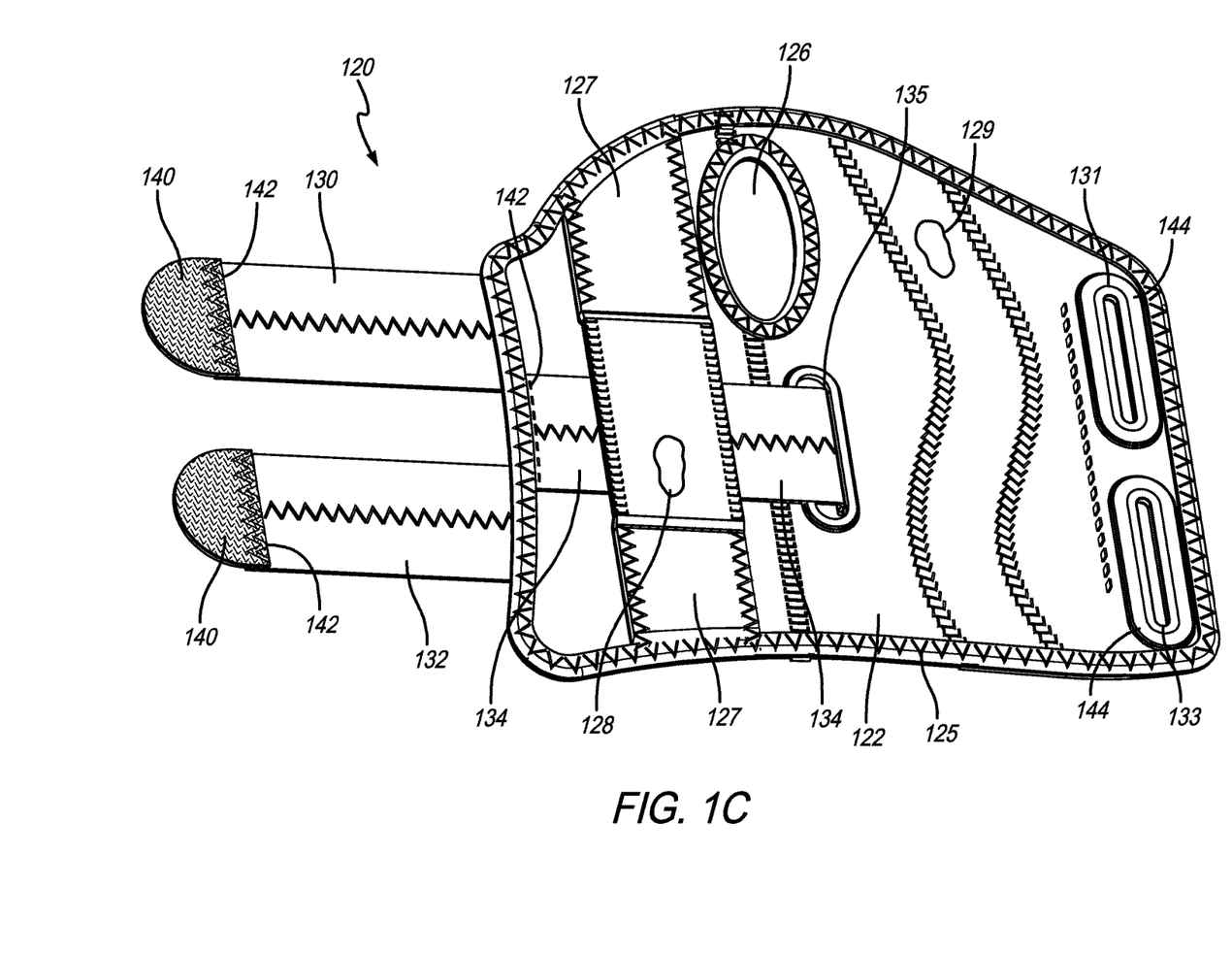
FIG. 1C is a plan view of the wrist brace of FIG. 1A, laid flat to expose the interior surface of the brace and with the fastening sleeve removed to show the third strap.

Referring to the drawings, FIGS. 1A-1C show a wrist brace 120 according to the present invention. The wrist brace 120 includes a base member 122 made by cutting planar sheets of one or more elastomeric materials into the desired shape. The exterior surface of the base member 122 is preferably covered with fabric bearing fiber loops 124 that adheres to hook-type material when the fiber loops and hook-type material are pressed together. The base may include base edge binding 125.

The wrist brace 120 is formed to fit the human wrist and hand, and the base 122 has a thumb hole 126 to receive the thumb when worn. The wrist brace 120 may have a splint pocket 127 containing a rigid or flexible splint 128 shaped to fit the wrist and the palm of the hand when worn.

The wrist brace 120 also includes a first fastening strap 130, a second fastening strap 132, and a middle strap 134, which are preferably formed of a material that is somewhat elastic along the length of the straps. The base 122 includes a first aperture 131, a second aperture 133, and a middle aperture 135, all formed as reinforced apertures 144. The wrist brace 120 also includes a sleeve 136 for convenience of application.

Each of the first fastening strap 130, second fastening strap 132, and middle strap 134 terminates in a hook-type fastening tab 140 permanently fastened to the strap, for example by stitches 142. The fastening tabs 140 allows the straps to be tightened, and then detachably attached to the exterior surface of the base 122 to securely fasten the wrist brace on the wearer. Normally the first fastening strap 130 and the second fastening strap 132 are tightened first in order to secure the brace on the wrist and hand, then the middle strap 134 can be adjusted to provide the desired support to the palm.

Figure 2A:
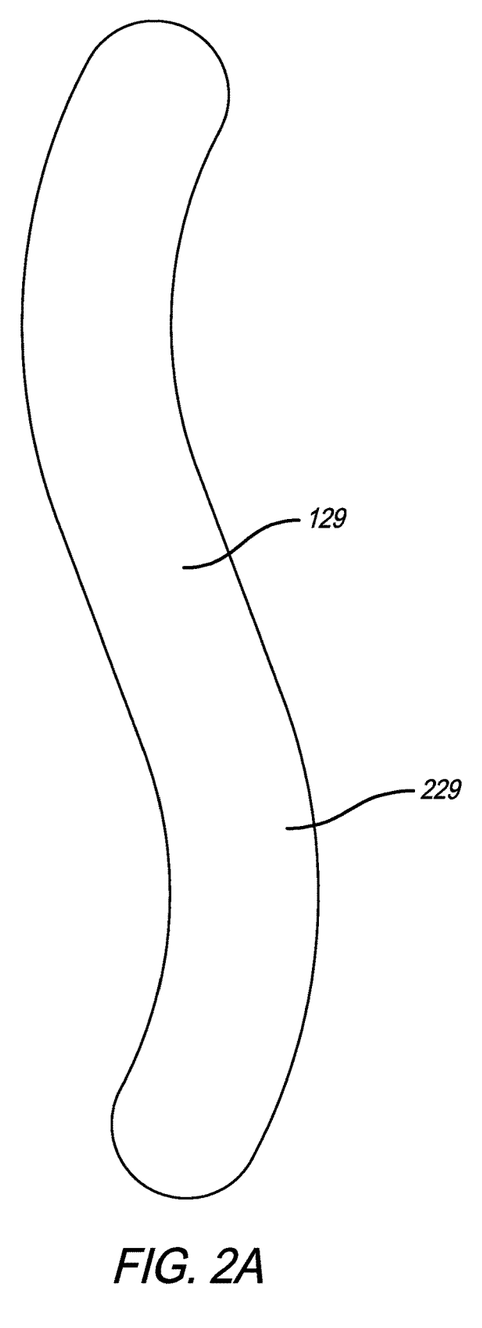
FIGS. 2A and 2B are front and side views of an outside support stay 129, 229 for use in the wrist brace of FIGS. 1-3 and 5A.
Figure 2B:
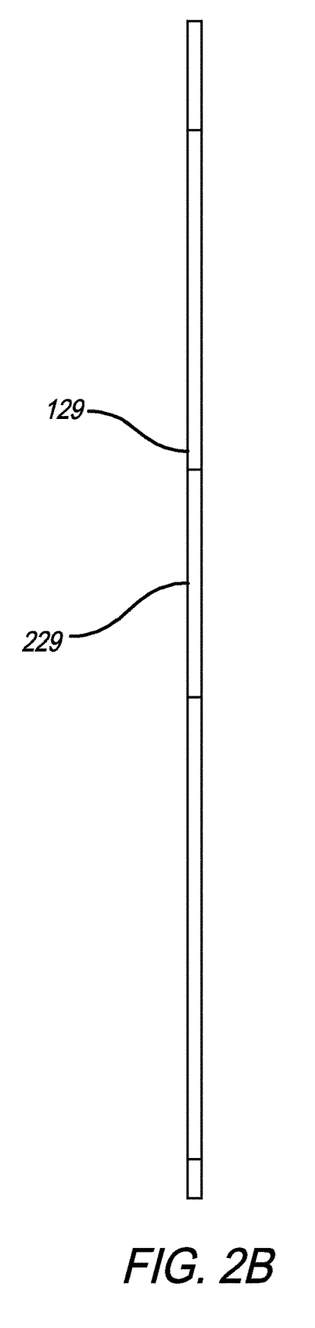

FIGS. 2A and 2B are front and side views of an outside support stay 129, 229 for use in the wrist brace of FIGS. 1-3 and 5A.

Figure 3A:
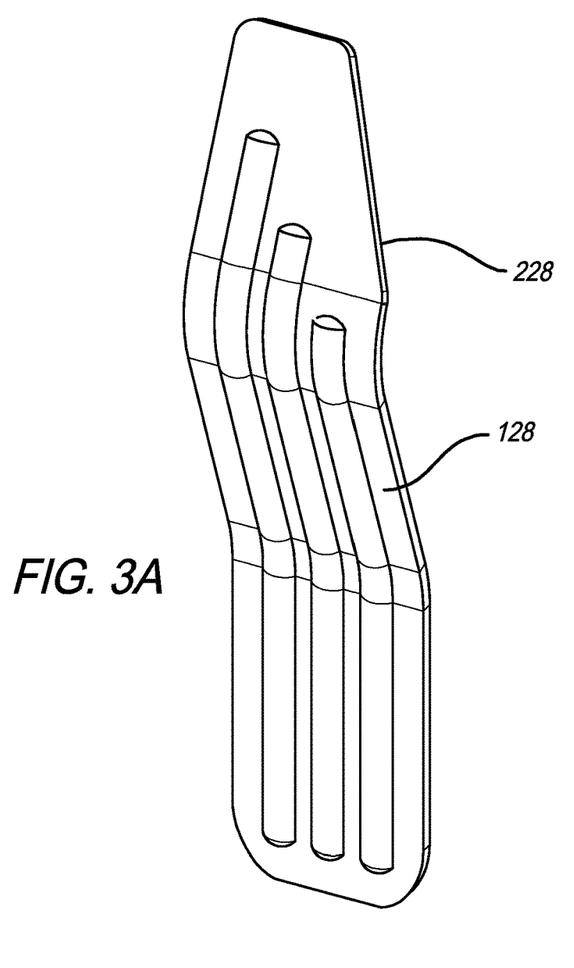
FIGS. 3A and 3B are perspective and cross-section views of a splint for use in the wrist brace of FIGS. 1-3.
Figure 3B:
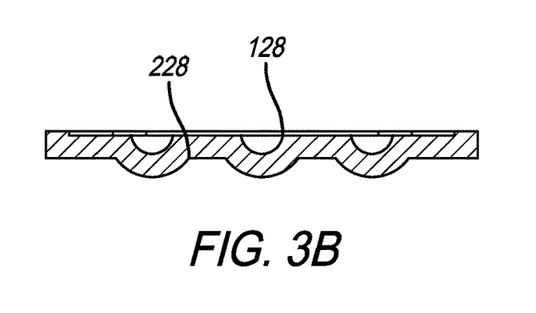
Figures 4A, 4B:
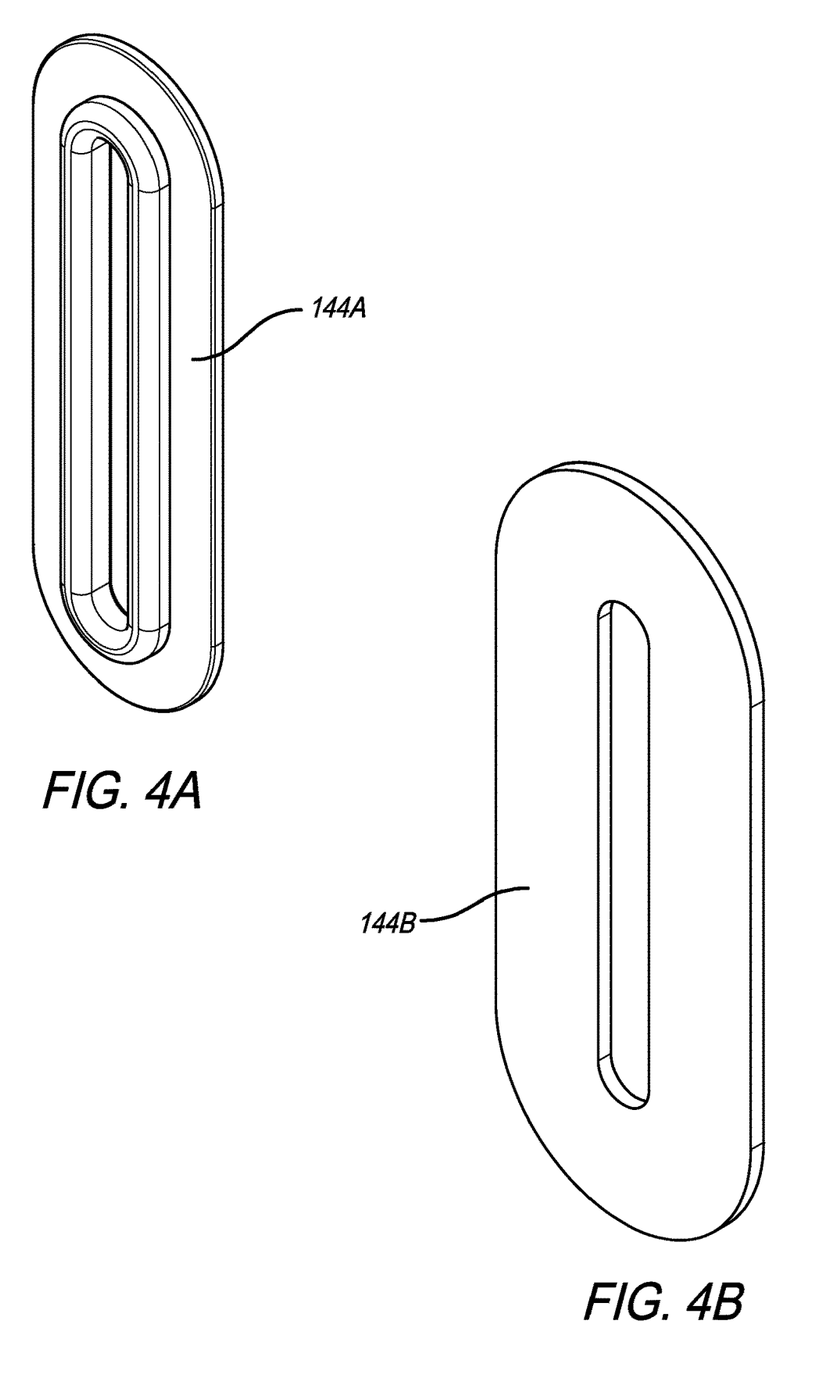
FIG. 4A is a perspective view of an aperture reinforcement base 144A for use in the wrist brace of FIGS. 1-3.
FIG. 4B is a perspective view of an aperture reinforcement backing 144B for use in the wrist brace of FIGS. 1-3.

FIGS. 3A and 3B are perspective and cross-section views of a splint for use in the wrist brace of FIGS. 1A-1C;

FIG. 4A is a perspective view of an aperture reinforcement base 144A for use in the wrist brace of FIGS. 1-3.

FIG. 4B is a perspective view of an aperture reinforcement backing 144B for use in the wrist brace of FIGS. 1-3.

Figure 5A:
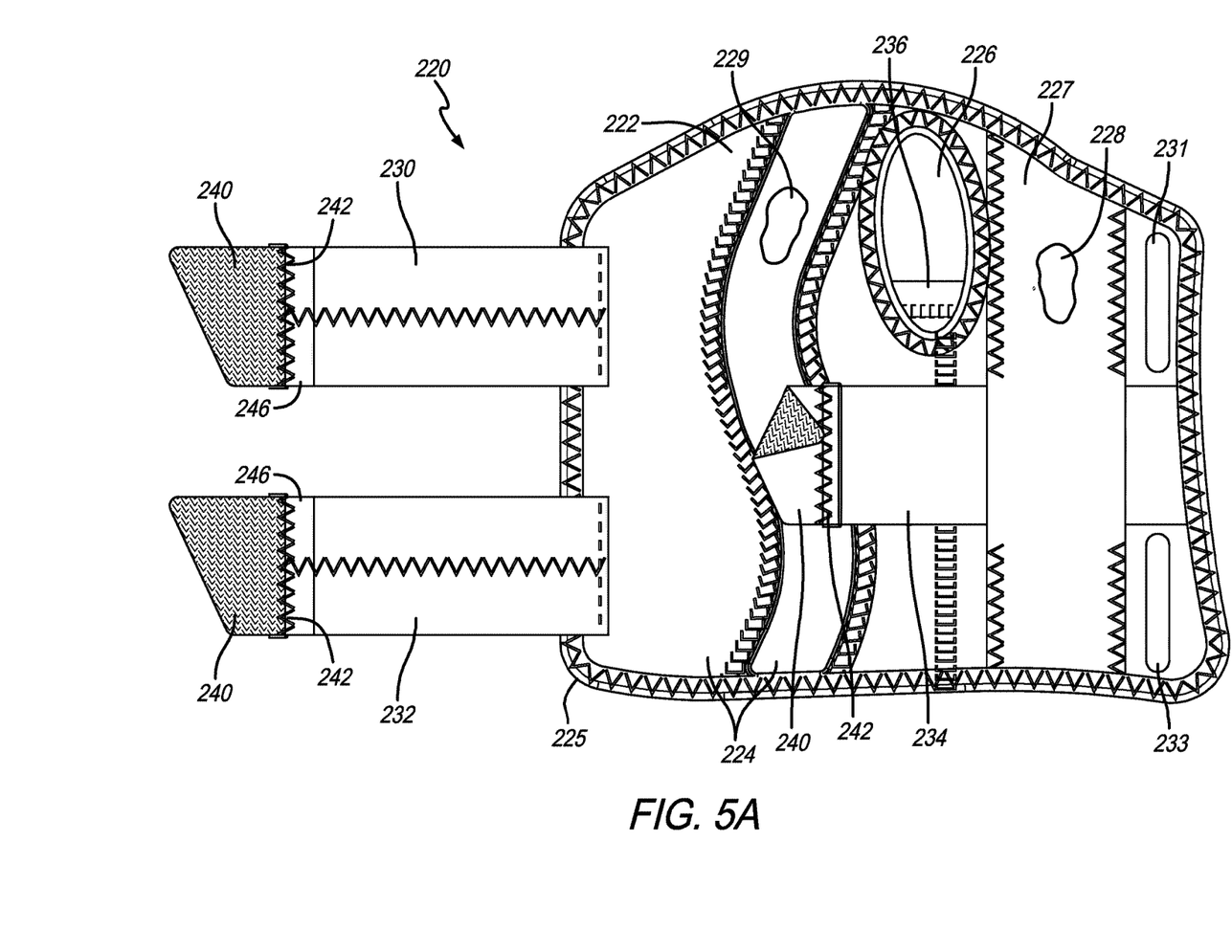
FIG. 5A is a plan view of an alternate wrist brace according to the invention, laid flat to expose the exterior surface of the brace.
Figure 5B:
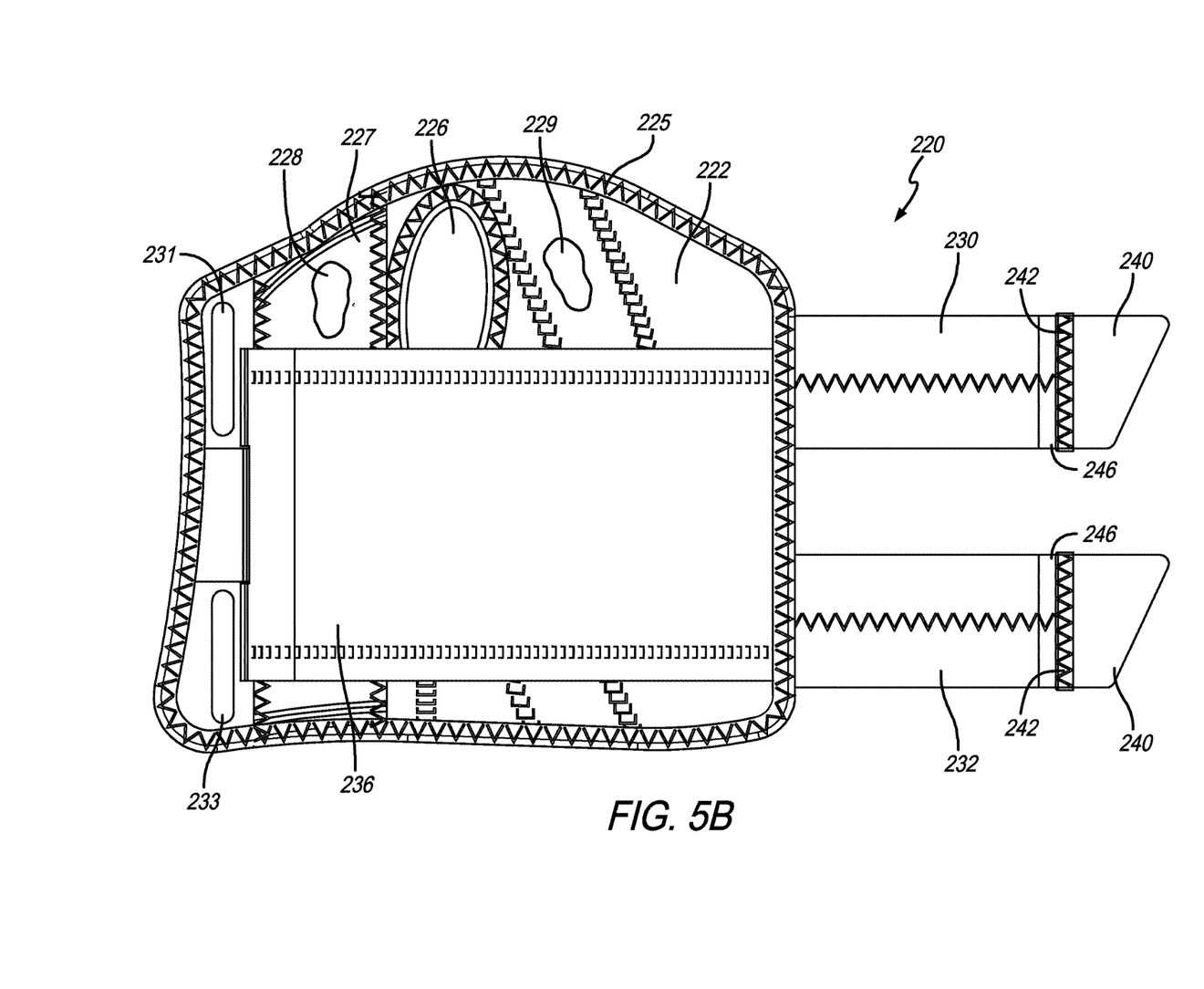
FIG. 5B is a plan view of the wrist brace of FIG. 5A, laid flat to expose the interior surface of the brace.
Figure 5C:
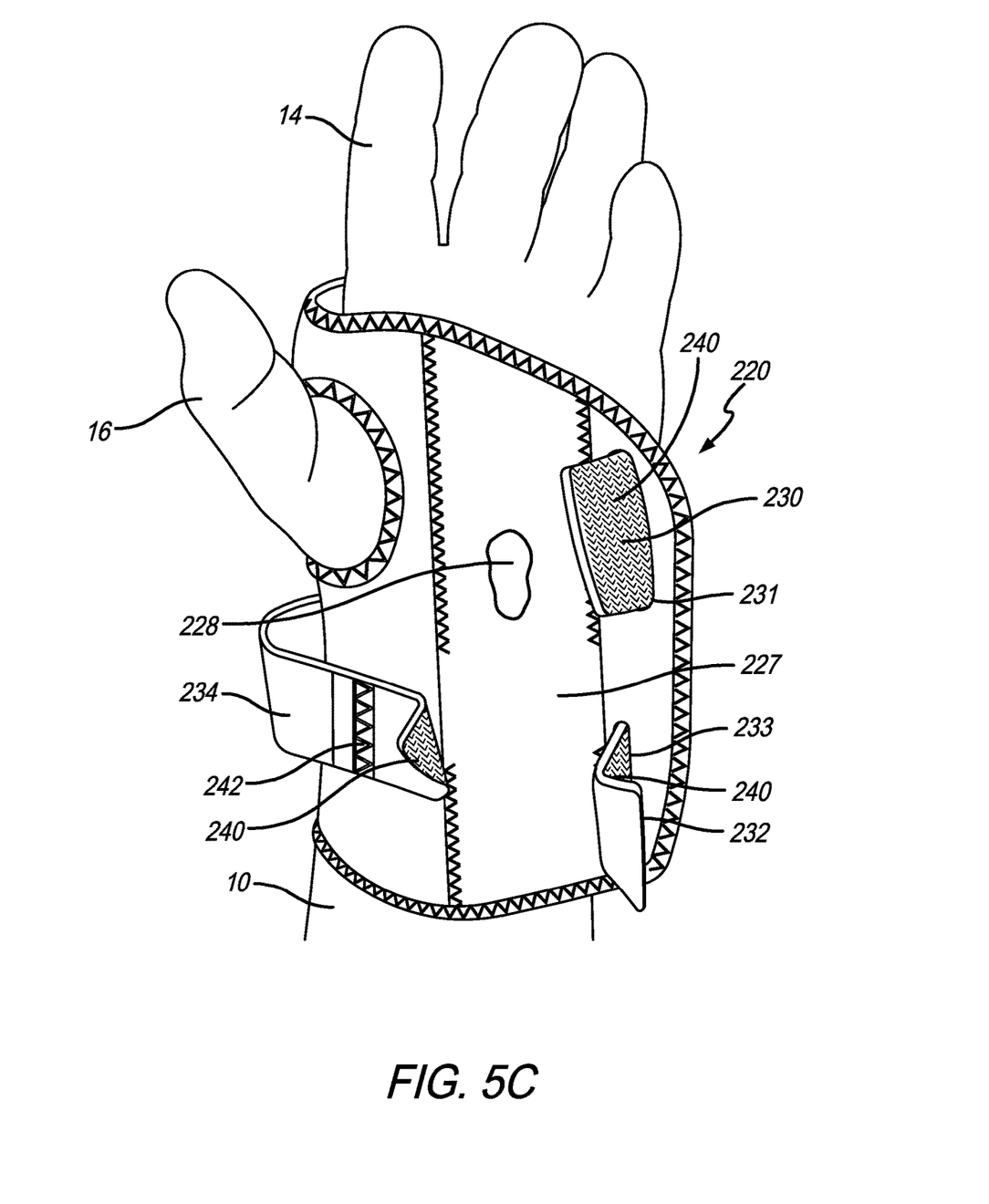
FIG. 5C is a perspective view of the palm side of the wrist brace of FIG. 5A applied to the wrist and hand of a person, with all the straps loose.

FIGS. 5A-5C show an alternate wrist brace 220 according to the present invention. The wrist brace 220 includes a base member 222 made by cutting planar sheets of one or more elastomeric materials into the desired shape. The exterior surface of the base member 222 is preferably covered with fabric bearing fiber loops 224 that adheres to hook-type material when the fiber loops and hook-type material are pressed together. The base may include base edge binding 225.

The wrist brace 220 may include one or more pockets to hold small items such as keys, access fobs, ID or credit cards, smart devices (for example fitness trackers) or visible flair 246 such as brightly colored items, reflectors, blinking lights, glow sticks, lighting, or reflective patches can be provided to enhance visibility of the wearer.

The wrist brace 220 is formed to fit the human wrist and hand between the forearm 10 and fingers 14, and the base 222 has a thumb hole 226 to receive the thumb 16 when worn. The wrist brace 220 may have a splint pocket 227 containing a rigid or flexible splint 228 shaped to fit the wrist and the palm of the hand when worn.

The wrist brace 220 also includes a first fastening strap 230, a second fastening strap 232, and a middle strap 234, which are preferably formed of a material that is somewhat elastic along the length of the straps. The base 222 includes a first aperture 231 and a second aperture 233, both formed as reinforced apertures. The wrist brace 220 also includes a sleeve 236 for convenience of application.

Each of the first fastening strap 230, second fastening strap 232, and middle strap 234 terminates in a hook-type fastening tab 240 permanently fastened to the strap, for example by stitches 242. The fastening tab 240 allows the straps to be tightened, and then detachably attached to the exterior surface of the base 222 to securely fasten the wrist brace on the wearer.

Figure 5D:
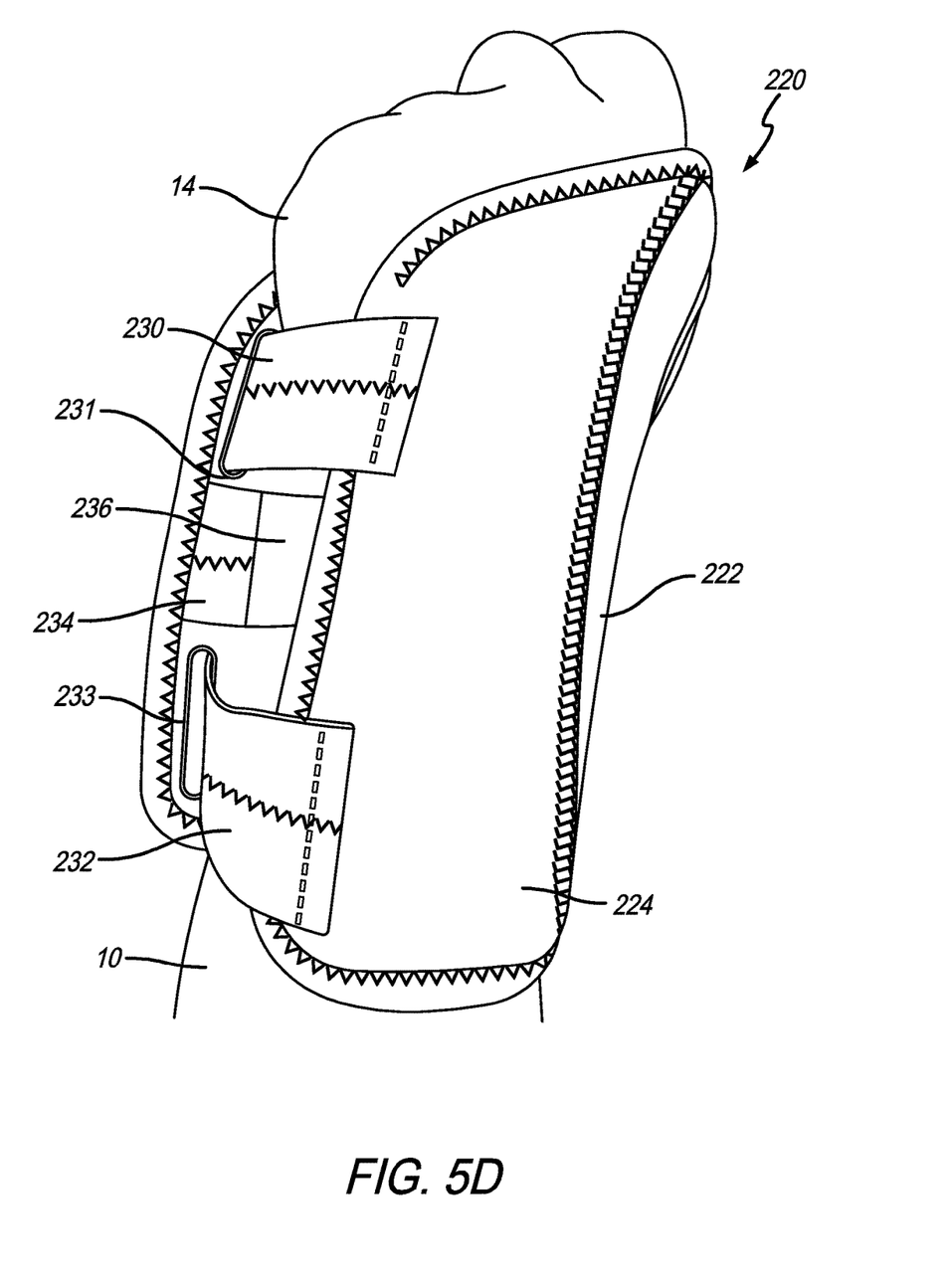
FIG. 5D is a perspective view of the back side of the wrist brace of FIG. 5A applied to the wrist and hand of a person, with all the straps loose.

FIGS. 5C and 5D show the wrist brace 220 applied to the hand of a person, with all the straps loose so the brace 220 is loosely retained on the hand by the sleeve 236 and base 222. This is the first step in applying the brace to a person.

Figure 5E:
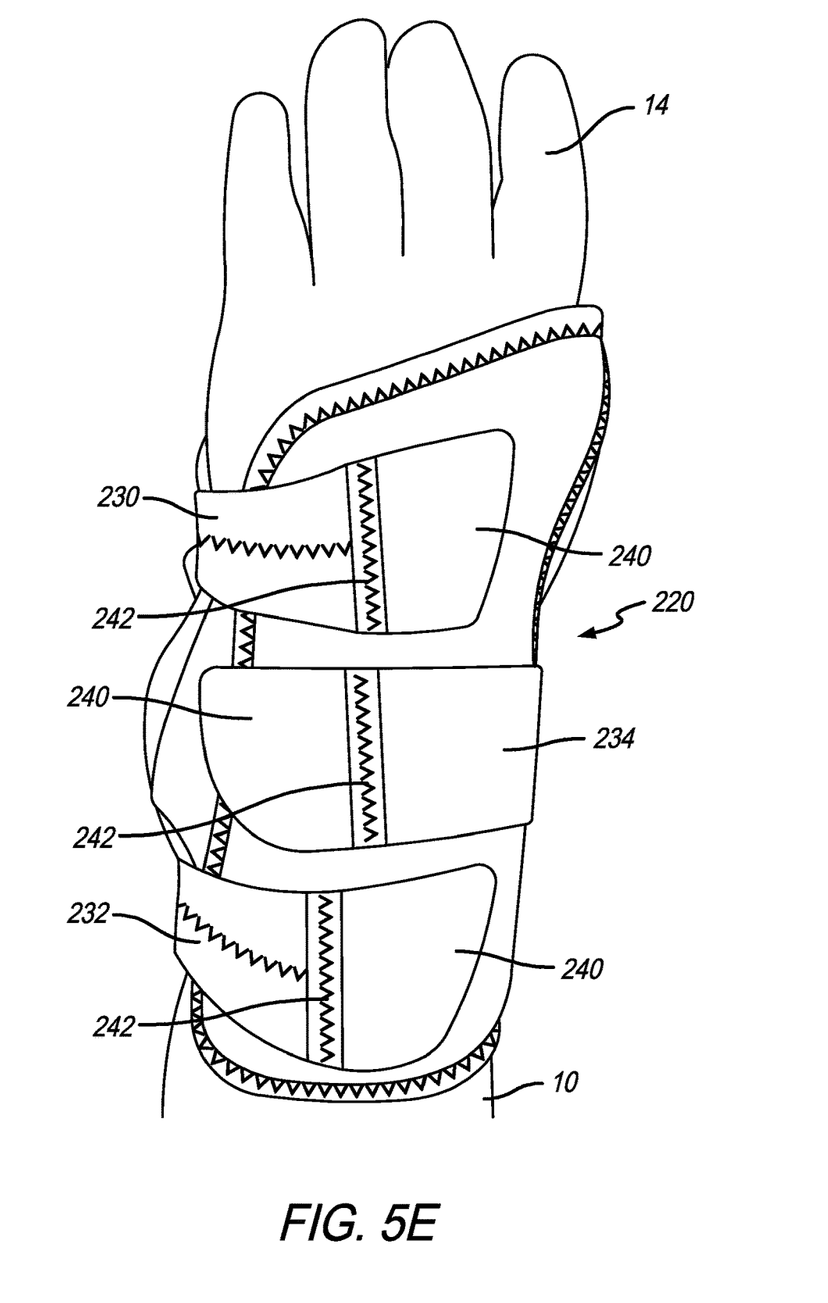
FIG. 5E is a perspective view of the back side of the wrist brace of FIG. 5A applied to the wrist and hand of a person, showing all the straps fastened down.
Figure 5F:
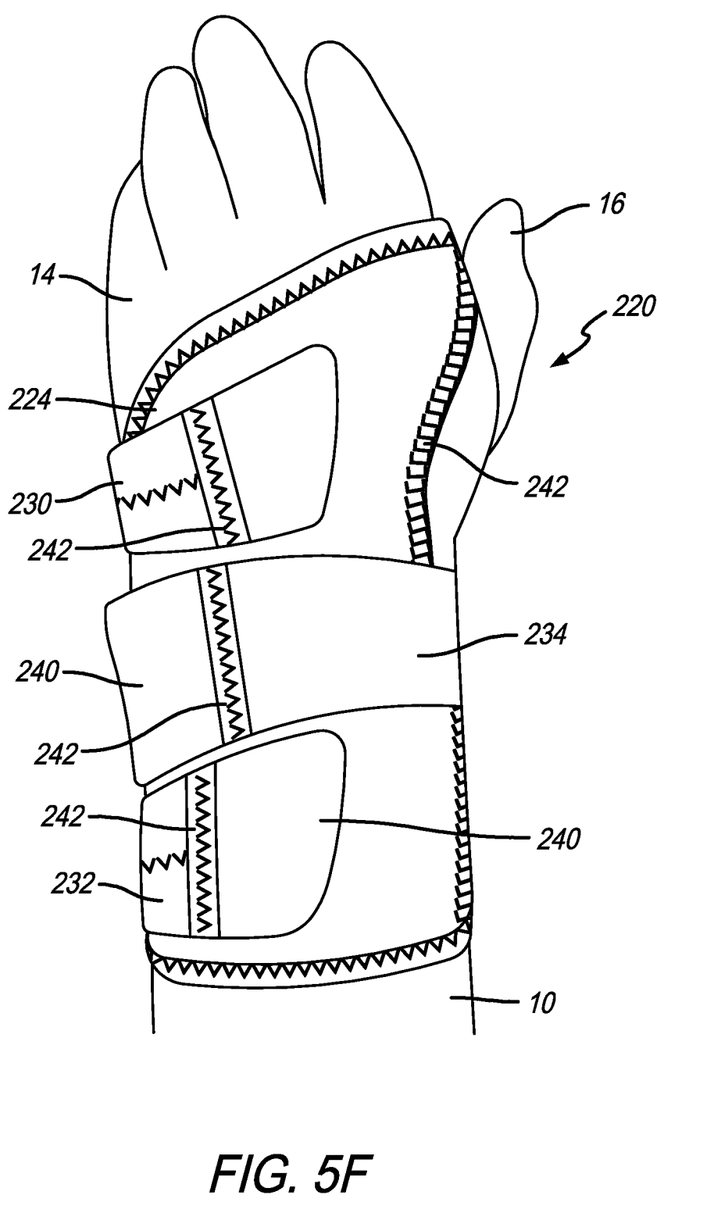
FIG. 5F is a second perspective view of the back side of the wrist brace of FIG. 5A applied to the wrist and hand of a person, showing all the straps fastened down.
Figure 5G:
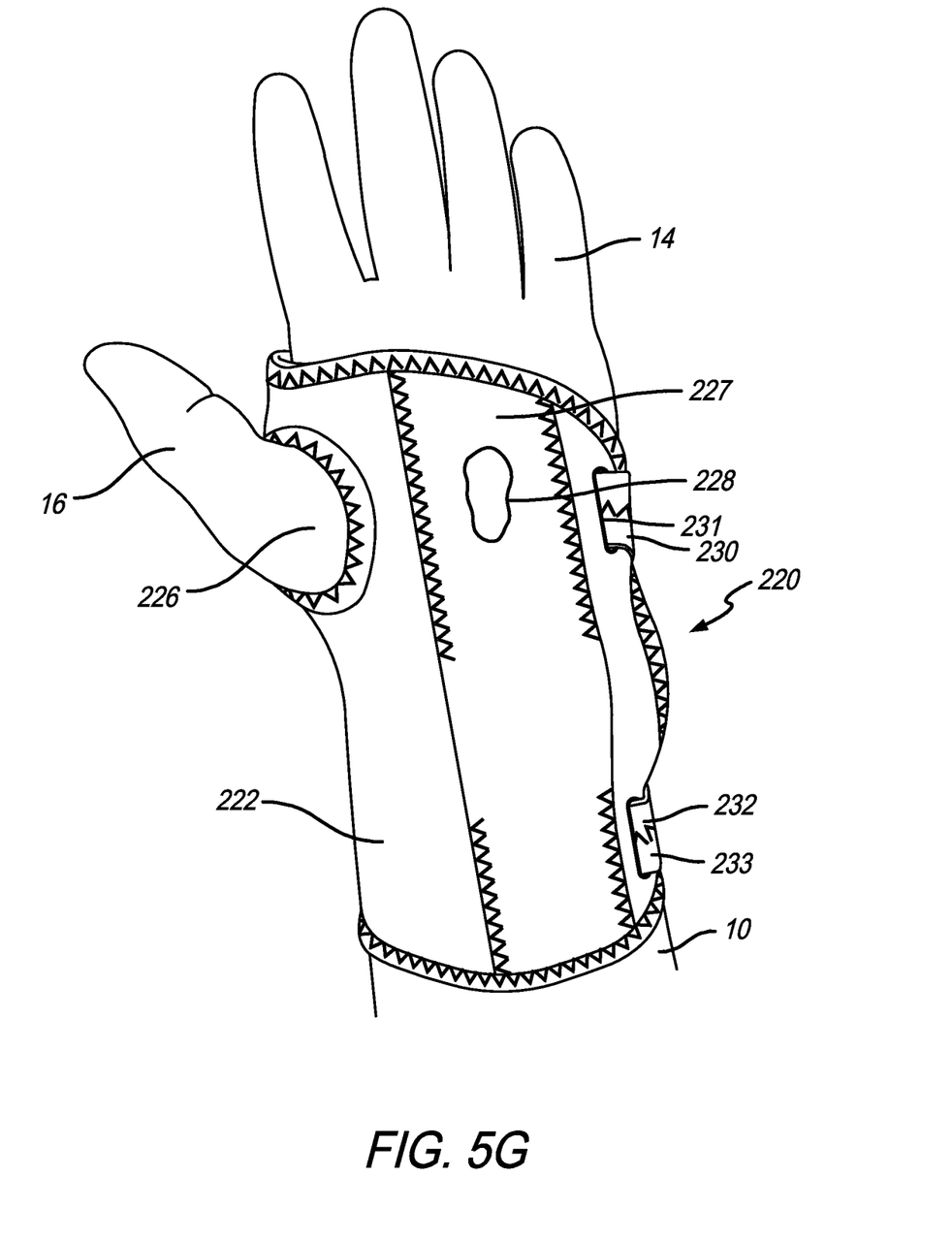
FIG. 5G is a perspective view of the palm side of the wrist brace of FIG. 5A applied to the wrist and hand of a person, with all the straps fastened down.

FIGS. 5E, 5F, and 5G show the wrist brace 220 applied to the wrist and hand of a person, with all the straps fastened down. Normally the first fastening strap 230 and the second fastening strap 232 are tightened first in order to secure the brace on the wrist and hand, then the middle strap 234 can be adjusted to provide the desired support to the palm. Advantageously, all the strap ends align at the same general location when tightened and fastened down. This makes it easier to iteratively adjust the tension in the straps, to achieve maximum comfort and support for that particular wearer of the wrist brace.

It is understood that the invention is not confined to the embodiments set forth herein as illustrative, but embraces all such forms thereof that come within the scope of the following claims.

What is claimed is:

1. A wrist brace, comprising:
   (a) a base wearable in snug covering relationship to portions of the hand and wrist of a person, the base having an interior surface and an exterior surface, the base having a thumb hole, a first aperture, a second aperture, and a middle aperture;
   (b) a splint having portions adjacent to the interior surface of the base and shaped to fit the palm of a person;
   (c) a first fastening strap, a second fastening strap, and a middle strap, each strap having a free end;
   wherein the middle strap has a fixed end permanently attached to the interior surface of the base and extending inside the base to a middle portion positioned between the interior surface of the base and the splint to press the splint against the palm when the middle strap is placed under tension, and wherein the free end of the middle strap extends inside the base and through the middle aperture when worn by a person; and
   wherein the first fastening strap extends through the first aperture and the second fastening strap extends through the second aperture when worn by a person.

2. The wrist brace of claim 1, wherein a loop material is permanently fastened to at least a portion of the exterior surface of the base, and wherein a hook material is permanently fastened to the free ends of each of the first fastening strap, the second fastening strap, and the middle strap, whereby the free ends of the straps may be detachably attached to the exterior surface of the base.

* * * * *